United States Patent
Wood et al.

(10) Patent No.: US 8,266,753 B2
(45) Date of Patent: Sep. 18, 2012

(54) MOUNTED BEAM BRUSHHEAD FOR TRANSVERSE DRIVE POWER TOOTHBRUSH

(75) Inventors: Jerry C. Wood, Fall City, WA (US); Duane Kutsch, Scottsdale, AZ (US); Joseph W. Grez, North Bend, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1061 days.

(21) Appl. No.: 11/814,055

(22) PCT Filed: Dec. 9, 2004

(86) PCT No.: PCT/IB2004/052737
§ 371 (c)(1),
(2), (4) Date: Sep. 5, 2008

(87) PCT Pub. No.: WO2005/058190
PCT Pub. Date: Jun. 30, 2005

(65) Prior Publication Data
US 2009/0000797 A1 Jan. 1, 2009

Related U.S. Application Data

(60) Provisional application No. 60/528,638, filed on Dec. 11, 2003.

(51) Int. Cl.
*A61C 17/22* (2006.01)
(52) U.S. Cl. ............................. 15/22.1; 15/22.2; 310/80
(58) Field of Classification Search ................... 15/22.1, 15/22.2, 22.4, 23, 24, 21.1; 310/80, 81
See application file for complete search history.

(56) References Cited

U.S. PATENT DOCUMENTS

| | | | | |
|---|---|---|---|---|
| 5,189,751 A | * | 3/1993 | Giuliani et al. | ................. 15/22.1 |
| 5,263,218 A | | 11/1993 | Giuliani et al. | |
| 5,378,153 A | * | 1/1995 | Giuliani et al. | ............... 433/216 |
| 6,140,723 A | * | 10/2000 | Matsui et al. | .................... 310/81 |
| 2003/0204924 A1 | * | 11/2003 | Grez et al. | ..................... 15/22.1 |

* cited by examiner

*Primary Examiner* — Shay Karls

(57) ABSTRACT

The resonator assembly for a power toothbrush includes an elongated solid rod made from stainless steel, having a back assembly which includes permanent magnets which interact with an electromagnet in a drive system in the handle of the toothbrush to produce a transverse motion of the rod. A mount member is connected to the rod at a selected point along its length, and is mounted to a toothbrush housing so that the rod resonates about the mount member at a selected frequency.

6 Claims, 1 Drawing Sheet ized metal rod 40 which in the embodiment shown functions as the drive shaft 21 and is made from stainless steel, but could also be made from other materials, including

MOUNTED BEAM BRUSHHEAD FOR TRANSVERSE DRIVE POWER TOOTHBRUSH

CROSS REFERENCE TO RELATED APPLICATION

This application claims the benefit of U.S. provisional application Ser. No. 60/528,638 filed 11 Dec. 2003, which is incorporated herein by reference.

TECHNICAL FIELD

This invention relates generally to power toothbrushes, and more specifically concerns a resonator structure for a transverse drive power toothbrush.

BACKGROUND OF THE INVENTION

Many power toothbrushes which operate at or near a resonant frequency associated with the toothbrush structure have structurally complicated resonator assemblies. The drive system for the toothbrush, usually located in the handle, produces a movement of the resonator assembly, which includes a mounting shaft or similar member having a brushhead mounted on a distal end thereof. The resonator assembly includes a mounting element to the toothbrush housing, for example, a torsion pin or other spring member. Many resonator assemblies, however, while often providing effective results, such as that shown in U.S. Pat. No. 5,378,153, must be manufactured and mounted with substantial precision, requiring a careful and expensive manufacturing process.

Further, the physical connection, for instance brazing, between the various parts of the resonator assembly, can be defective, leading to breakage and/or reduced performance. Such a resonator assembly also frequently requires a number of individual parts. The individual parts must be connected in such a way that the assembly resonates at the preselected resonant frequency, within a relatively close tolerance (+5 Hz).

It is desirable that improvements be made in the cost and reliability of such a resonator system, without sacrificing the performance thereof.

BRIEF SUMMARY OF THE INVENTION

Accordingly, the present invention is a resonator assembly for a power toothbrush having a drive system comprising: an elongated drive member, having a back assembly at a rear end thereof, cooperating with the drive system to move the driven member, the driven member being adapted to receive a workpiece at a distal end thereof; and a mount member which mounts the driven member to a toothbrush housing so that the driven member moves about the mount member at a selected frequency.

DETAILED DESCRIPTION OF THE INVENTION

Figure 1:
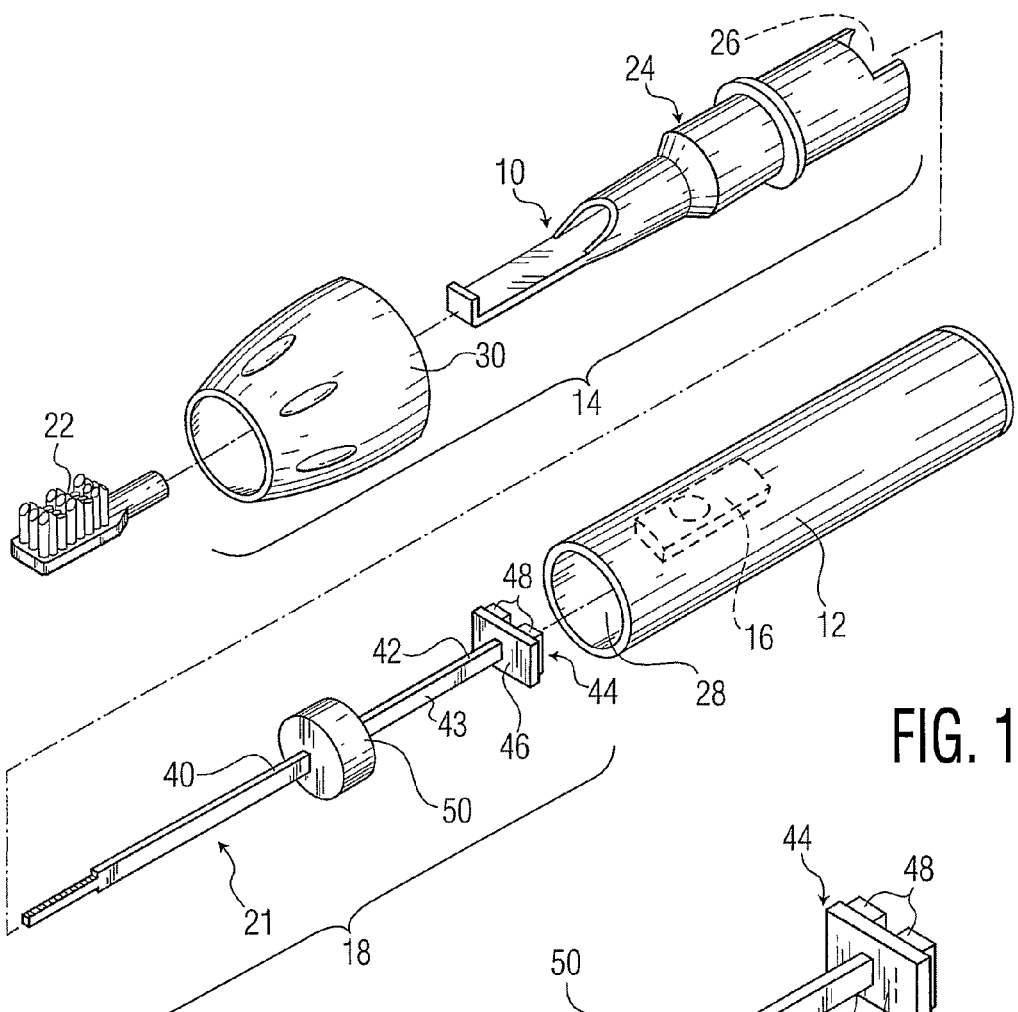
FIG. 1 is an exploded view which includes the beam-type brushhead of the present invention.

FIG. 1 shows a complete power toothbrush 10 which includes a handle portion 12 and a head portion 14, which is attached to the handle portion 12 in some manner, such as by mating threaded sections or clips or some other similar structure. Toothbrush 10 also includes a drive assembly shown generally at 16 in the handle portion 12 of the toothbrush, the drive assembly cooperatively working with a resonator assembly 18, which typically will include a drive shaft 21 on which a workpiece such as a toothbrush brushhead 22 is located.

In the embodiment shown, head portion 14 also includes a mounting assembly 24 which surrounds the resonator assembly 18, including the drive shaft 21. A rear end portion 26 of the mounting assembly 24 fits into a mating front portion 28 of the handle. A nut 30 is used to securely attach the mounting assembly 24 with the resonator to the handle 12.

Figure 2:
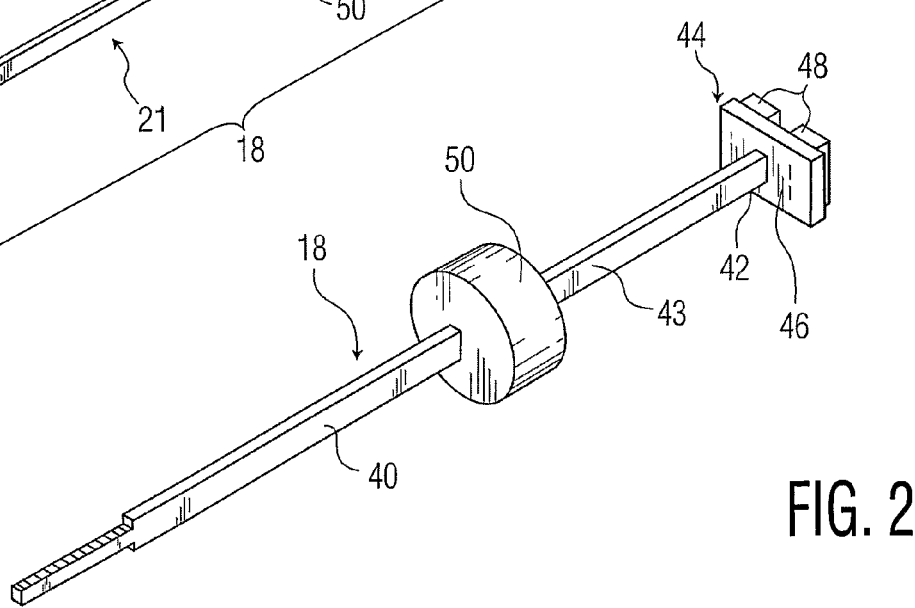
FIG. 2 shows the resonator portion of the assembly of FIG. 1.

Resonator assembly 18, is shown in more detail in FIG. 2. In the embodiment shown, resonator assembly 18 includes an elongated metal rod 40 which in the embodiment shown functions as the drive shaft 21 and is made from stainless steel, but could also be made from other materials, including spring steel, and in another embodiment a thermoplastic material. In the embodiment shown, the rod is approximately 3.75 inches long by 0.125 inches wide and 0.75 inches thick. The rod 40 could be solid or hollow, like a tube.

At a rear end 42 of rod 40 is a back assembly 44, which includes a small iron plate 46, upon which are mounted a pair of permanent magnets 48-48. In the embodiment shown, permanent magnets 48-48 cooperatively work with an electromagnet portion of drive system 16 to produce a back-and-forth (transverse) movement of back assembly 44, including the rear portion 43 of rod 40. Such a driving arrangement is shown in detail in U.S. Pat. No. 5,189,751, the contents of which are hereby incorporated by reference. At a selected point along the length of rod 40 is a mounting member 50. In the embodiment shown, the mounting member 50 is located approximately 1.5 inches from the rear end 42 of rod 40. The mounting member is a urethane cylinder into which rod 40 is pressed.

Mounting member 50 in turn is pressed into the mounting assembly 24. In the embodiment shown, the mounting member 50 is 60-75 shore-D material. It is approximately 0.5 inches in diameter and 0.375 inches thick. These dimensions, however, can be varied. The mounting member 50 could alternatively be made from hard metal, such as steel, or thermoplastic material. The durometer of the mounting member in one embodiment is selected to provide a particular Q for the appliance. The mounting member further can be changed by changing the material or its position along the rod 40 to give a desired frequency of performance and amplitude of brushhead movement.

Further, the arrangement can be used to guide the user with respect to the proper amount of force applied by the user on the toothbrush against the teeth. If the force applied is too large or too small, very little or no amplitude of the brush results. When the force applied by the user is just right, an effective, desirable amplitude of the brush movement results.

In operation, the single beam rod 40 acts as a spring member for the toothbrush, resonating about mount element 50, which will typically move a small amount. With the resonator rod 40 mounted as shown, and a drive arrangement comprising an electromagnet and the backplate 44 with permanent magnets on the rear end of rod 40, a transverse (back-and-forth action) of rod 40 results, with the distal end of the rod, i.e. the end upon which the brush 22 is mounted, moving in an opposite direction to the movement of the rear portion 43 of the rod 40.

The advantages of the resonator structure as shown are that it can be manufactured as a precision part relatively easily and inexpensively; further, it has good repeatability and reliability. There is no dependence upon brazing connections to other parts. Hence, the single beam resonator has manufacturing and operating advantages over other resonator structures.

Although a preferred embodiment of the invention has been disclosed for purposes of illustration, it should be understood the various changes, modifications and substitutions may be incorporated in the embodiment without departing from the spirit of the invention is defined by the claims as follows:

The invention claimed is:

1. A resonator assembly for a power toothbrush having a handle portion and a head portion having a mounting assembly, the mounting assembly fitting into a mating portion of the handle portion, the handle portion having a drive system, comprising:

an elongated single beam rod member, having a back assembly at a rear end thereof, cooperating with the drive system to move a proximal end of the rod member in a back and forth transverse direction, the rod member being adapted to receive a workpiece at a distal end thereof; and a mount member which surrounds and mounts the rod member to the mounting assembly, wherein the mount member has a substantially circular periphery surrounding the rod member for pressing contact with the mounting assembly, the mounting member being movable along the rod member to provide a desired frequency of performance and amplitude of brushhead movement wherein the distal end of said rod member accordingly moves about the mount member in a back and forth transverse direction opposite to that of the proximal end thereof at a selected frequency.

2. The assembly of claim 1, wherein the rod member is solid.

3. The assembly of claim 2, wherein the rod member is metal, and wherein the mount member is urethane, having a 60-75 shore-D durometer rating.

4. The assembly of claim 2, wherein the back assembly includes a plate and a plurality of permanent magnets, which interact with an electromagnet in the drive system to produce a transverse motion of the rod member.

5. The assembly of claim 1, wherein the rod member is hollow.

6. The assembly of claim 1, wherein the rod member is a plastic material.

* * * * *